United States Patent
Yang et al.

(10) Patent No.: US 7,608,630 B2
(45) Date of Patent: Oct. 27, 2009

(54) MARASMIUS ANDROSACEUS L.ES FR EXTRACT, PIPERIDONE DERIVATIVE, AND THEIR USE FOR THE PREPARATION OF HYPERTENSIVES

(75) Inventors: Jichu Yang, Beijing (CN); Nan Wang, Beijing (CN); Xing Yang, Beijing (CN); Jianping Ren, Beijing (CN)

(73) Assignees: Hainan Yangpu New Special Pharmaceutical Co., Ltd., Haikou (CN); Beijing Toulin Medicine Science and Technology Co., Ltd., Beijing (CN)

( * ) Notice: Subject to any disclaimer, the term of this patent is extended or adjusted under 35 U.S.C. 154(b) by 0 days.

(21) Appl. No.: 10/587,824

(22) PCT Filed: Sep. 29, 2004

(86) PCT No.: PCT/CN2004/001125

§ 371 (c)(1),
(2), (4) Date: Sep. 14, 2006

(87) PCT Pub. No.: WO2005/075423

PCT Pub. Date: Aug. 18, 2005

(65) Prior Publication Data

US 2007/0160625 A1 Jul. 12, 2007

(30) Foreign Application Priority Data

Jan. 30, 2004 (CN) .................. 2004 1 0001071

(51) Int. Cl.
*A61K 31/4412* (2006.01)
(52) U.S. Cl. .................................................. 514/345
(58) Field of Classification Search .................. None
See application file for complete search history.

(56) References Cited

U.S. PATENT DOCUMENTS 5,939,436 A 8/1999 Carling et al.

FOREIGN PATENT DOCUMENTS

| CN | 1261363 A | 7/2000 |
| CN | 1356982 A | 7/2002 |
| CN | 1363297 A | 8/2002 |
| HU | 44495 A2 * | 3/1988 |

OTHER PUBLICATIONS

Howton, David R., "1,3-Dimethylpiperidone-4," *Journal of Organic Chemistry*, 1945, vol. 10, pp. 277-282.
Mannich, C., et al., "Uber 3,5-alkylierte 4-oxo-piperidine," *Berichte Der Deutschen Chemischen Gesellschaft*, 1936, vol. 69b, pp. 2299-2305.

* cited by examiner

*Primary Examiner*—Taofiq A Solola
(74) *Attorney, Agent, or Firm*—Alston & Bird LLP

(57) ABSTRACT

The present invention relates to Marasmius androsaceus L.es Fr extract, a compound of formula I, or pharmaceutically acceptable salts thereof, and to methods for their preparation, pharmaceutical composition comprising the same as well as use of the extract or the compound in the preparation of a medicament for the prevention and/or treatment of hypertension and its related diseases.

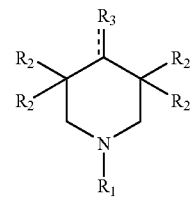

9 Claims, No Drawings

MARASMIUS ANDROSACEUS L.ES FR EXTRACT, PIPERIDONE DERIVATIVE, AND THEIR USE FOR THE PREPARATION OF HYPERTENSIVES

TECHNICAL FIELD

The present invention relates to *Marasmius androsaceus* L.es Fr extract, piperidone derivative, and methods for their preparation as well as use of the same for the preparation of antihypertensives.

BACKGROUND ART

Hypertension and its related diseases are one kind of diseases seriously threaten human health and lives. Numerous peoples are suffering from it, and the patient tends to be younger in recent years. Although human has developed various drugs for the prevention and treatment of hypertension, it is still urgent to exploit new type of effective hypotensors.

CONTENTS OF THE INVENTION

The present inventors have been discovered by research that *Marasmius androsaceus* L.es Fr extract and piperidone derivative having the following formula I had very notable effect of reducing blood pressure, and thus could be used in the preparation of a medicament for prevention and/or treatment of hypertension and its related diseases.

Therefore, the first aspect of the present invention relates to *Marasmius androsaceus* L.es Fr extract, characterized by comprising 3,3,5,5-tetramethyl-4-piperidone, i.e., a compound of the following formula II.

In a second aspect the present invention provides a compound of the following formula I or a pharmaceutically acceptable salt thereof:

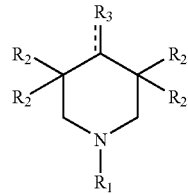

wherein, $R_1$ and each of $R_2$, the same or different, independently represent hydrogen atom or $C_1$-$C_5$ alkyl;

===== represents a single bond or a double bond, when ===== is a double bond, $R_3$ is oxygen atom; when ===== is a single bond, $R_3$ is hydroxyl group.

In a third aspect the present invention relates to a method for the preparation of *Marasmius androsaceus* L.es Fr extract, which comprises extracting fungi *Marasmius androsaceus* L.es Fr mycelium with an organic solvent, an aqueous organic solvent or water, and concentrating the resultant extractive to obtain the extract.

In a fourth aspect the present invention provides a method for the preparation of a compound of formula I, which comprises extracting, e.g., fungi *Marasmius androsaceus* L.es Fr mycelium with an organic solvent, an aqueous organic solvent or water to obtain an extract, separating and purifying the extract thereby obtaining a compound monomer of formula II, and then deriving the compound monomer by reacting it with a calculated amount of alkyl halide under basic condition.

In a fifth aspect the present invention relates to a pharmaceutical composition comprising as an active ingredient *Marasmius androsaceus* L.es Fr extract, or a compound of formula I, or a pharmaceutically acceptable salt thereof, and one or more pharmaceutically acceptable carriers or excipients.

In a sixth aspect the present invention relates to use of *Marasmius androsaceus* L.es Fr extract or a compound of formula I in the preparation of a medicament for the prevention and/or treatment of hypertension and its related diseases.

In one preferred embodiment of the present invention, the compound of formula I is a compound of formula I wherein $R_1$ is hydrogen, each of $R_2$ is methyl, ===== is a double bond and $R_3$ is oxygen atom, i.e., the compound of the following formula II:

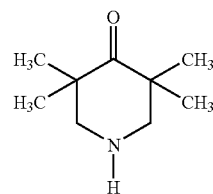

*Marasmius androsaceus* L.es Fr is dried mycelium of Tricholomataceae fungi *Marasmius androsaceus* L.es Fr. It is a type of edible fungi, and also a common Chinese medicine, and has the effects of, e.g., relaxing and activating the tendons and retinervus, and reliving pain.

According to the present invention, *Marasmius androsaceus* L.es Fr extract can be prepared according to the following method:

Fungi *Marasmius androsaceus* L.es Fr bacteria, as purchased from Institute of Microorganism, Chinese Academy of Sciende, with bacterial number of 5.512 a. Fermentation culturing

A culture medium is prepared by mixing the following components (by weight): bran 5%, glucose 4%, corn steep liquor 0.4%, magnesium sulfate 0.05%, and potassium dihydrogen sulfate 0.1%. A slant strain is transferred to the culture medium, and cultured at 22-26° C. for 7-8 days until forming sericate hypha and the culture medium becoming light yellow. The culture is stopped at pH=3.5-4.0.

b. The fermentation broth as above cultured is filtered to obtain mycelium.

c. The mycelium is extracted with an organic solvent, an aqueous organic solvent or water. The obtained extractive is filtered and concentrated thereby obtaining *Marasmius androsaceus* L.es Fr extract.

According to the present invention, the piperidone derivative of formula I can be prepared, as above described, by the steps of: extracting, e.g., fungi *Marasmius androsaceus* L.es Fr mycelium with an organic solvent, an aqueous organic solvent or water to obtain an extract, separating and purifying the extract thereby obtaining a compound monomer of formula II, and then suitably deriving the obtained compound monomer.

Particularly, the method for preparing the piperidone derivative of formula I further comprises the following steps on the basis of the above steps a-c for preparing the *Marasmius androsaceus* L.es Fr extract:

d. The resultant extract is separated by chromatography with a silica gel column, and undergone gradient elution using chloroform:methanol=1-100%; 80-90% of the chloroform fraction is collected to obtain a refined product of the compound of formula II; then, the resultant product is repetitively recrystallized with ethyl acetate/methanol thereby obtaining a compound monomer of formula II.

e. The compound of formula II is dissolved in a pH=8-12 alkali methanol solution, to which a calculated amount of alkyl halide is added; the system undergoes reaction at 40-60° C. for 10 h; then, the resultant reaction product is concentrated, and repetitively recrystallized thereby obtaining the compound of formula I.

In the step c of the above methods for preparing *Marasmius androsaceus* L.es Fr extract and the compound of formula I, the organic solvent used includes alcohols such as methanol, ethanol, propanol and butanol; alkyl halides such as dichloromethane and trichloromethane; esters such as methyl acetate, ethyl acetate and propyl acetate; and also ethers such as petroleum ether and diethyl ether. The preferred solvent is chloroform.

Pharmacological study shows that the extract of the present invention characterized by comprising the compound of formula II, the refined product thereof, i.e., the compound monomer of formula II, as well as the derived product of the compound of formula II, i.e., the compound of formula I all have very obvious effects of reducing blood pressure, which are mainly manifested themselves in that:

a. 50-100 mg/kg of the exact exhibits a very obvious effect of reducing blood pressure with respect to the models of anesthetic hypertensive rat and cat. 5-20 mg/kg of the compound of formula II exhibits a very obvious effect of reducing blood pressure with respect to the models of anesthetic rat and cat. 3-50 mg/kg of the compound of formula I exhibits a very obvious effect of reducing blood pressure with respect to the models of anesthetic rat and cat. All the effects of reducing blood pressure as above described can be maintained for above 4 h.

b. All the extract, the compound of formula II and the compound of formula I can inhibit the automatic rhythmic contraction of ileum section in guinea pig, which all can slowly relax smooth muscle within a concentration range of $5\times10^{-4}$ to $10\times10^{-2}$ mg/ml, until a complete relaxation within 3 to 5 min. The relaxation time may be up to 4-5 h (flushing once per 15 min). Isoprenaline at a concentration of $5\times10^{-5}$ mg/ml is used as a control, and the contraction inhibited thereby will be resumed in 20 min after flushing.

The above results show that the extract, the compound of formula II and the compound of formula I can inhibit the automatic rhythmic contraction of ileum section for an obviously longer time than isoprenaline as a control.

c. The extract, the compound of formula II and the compound of formula I all show significant effects on aorta smooth muscle of rabbit, which can inhibit the contraction of aorta smooth muscle of rabbit caused by adrenalin within a concentration range of $5\times10^{-4}$ to $10\times10^{-2}$ mg/ml, and will cause the relaxation of aorta smooth muscle of rabbit at a concentration of greater than $5\times10^{-5}$ mg/ml.

The above results show that the extract, the compound of formula II and the compound of formula I have good effects of relaxing smooth muscle and excellent effects of reducing blood pressure, with hold time greater than 4 h.

Therefore, the *Marasmius androsaceus* L.es Fr extract and the compound of formula I can be used in the preparation of a medicament for the prevention and/or treatment of hypertension and its related diseases, said hypertension and its related diseases including simple hypertension and coronary heart diseases caused by hypertension as well as other cardio- and cerebro-vascular diseases.

According to the present invention, the pharmaceutically acceptable salt of the compound described herein includes acid-addition salts formed with inorganic or organic acids therewith or base-addition salts formed with bases therewith. Wherein, the acid-addition salts include, but are not limited to, hydrochlorides, hydrobromides, hydroiodides, nitrates, sulfates, bisulfates, phosphates, biphosphates, acetates, propionates, butyrates, trimethylacetates, adipates, alginates, lactates, citrates, tartrates, succinates, maleates, fumarates, picrates, aspartates, gluconates, benzoates, mesylates, ethylsulfonates, benzenesulfonates, p-toluenesulfonates and pamoates; and the base-addition salts include, but are not limited to, ammonium salts, alkali metal salts such as sodium and potassium salts, alkaline earth metal salts such as calcium and magnesium salts; organic alkali salts such as dicyclohexyl amine and N-methyl-D-glucosamine salts, and amino acid salts such as arginine and lysine salts.

The *Marasmius androsaceus* L.es Fr extract or the compound of formula I of the present invention can be used alone, or in the form of a pharmaceutical composition by admixing it with a pharmaceutically acceptable carrier or excipient.

The pharmaceutical composition of the compound of the present invention can be administered by any of the following routes: oral, inhalation by spray, rectal, nasal, buccal, topical, parenteral such as injection or infusion by the routes of subcutaneous, intravenous, intramuscular, intraperitoneal, intrathecal, intraventricular, intrasternal and intracranial, or by the aid of an explanted container. In which, oral, injection or topical administration is preferred.

For oral administration, the compound of the present invention can be made into any of the dosage form suitable for oral administration, which include, but are not limited to, tablets, capsules, a solution or a suspension. Wherein, the carrier useful for tablets generally includes lactose and corn starch, to which a lubricant such as magnesium stearate may also be added. The diluent useful for capsule formulations generally includes lactose and dried corn starch. The aqueous suspension formulation is generally formed through mixing an active ingredient with suitable emulsifying agent and suspending agent. If desired, some sweetener, aromatizer or colorant may be further added to the above formulations for oral administration.

As to topical administration, in particular for the treatment of suffering surface or organ that is easily reached by topical application, such as the treatment of eyes, skin or lower enteric neurogenic diseases, the compound of the present invention can be made into different dosage form for topical administration according to different suffering surface or organ.

Particularly, for topical administration to the eyes, the compound of formula I of the present invention can be made into a dosage form of micronized suspension or solution, wherein the carrier used is isotonic sterile saline having a certain pH, to which an antiseptic such as chlorinated benzyl alkoxides may be added optionally. For ocular administration, the compound may also be made into ointments such as vaseline ointments.

For topical administration to the skin, the compound of formula I of the present invention can be made into a dosage in the form of ointments, lotions or creams, wherein an active ingredient is suspended or dissolved in one or more carries. The carrier useful for the ointment formulations includes, but is not limited to, mineral oil, liquid vaseline, petrolatum album, propylene glycol, polyethylene oxide, polypropylene oxide, emulsified wax and water. The carrier useful for the lotion or cream formulations includes, but is not limited to, mineral oil, sorbitan monostearic esters, Tween 60, palmitates, hexadecylene aromatic alcohol, 2-octyldodecanol, benzyl alcohol and water.

The compound of formula I of the present invention can also be administered in the form of sterile injection formulations, including sterile injection water or oil suspension or sterile injection solution. Wherein, the useable carrier and solvent include water, Ringer's solution and isotonic sodium chloride solution. In addition, sterile nonvolatile oil, e.g., monoglyceride and diglyceride, can also be used as solvent or suspending medium.

Further, the administration dosage and manner of the compound described therein depend on various factors, such as age, body weight, gender, natural health status and nutrient status of the patient, activity of the compound, administration time, metabolic rate, severity of the disease, and subjective judgment made by the physician. The preferred administration dosage is within 0.01-100 mg/kg body weight/day, and the most preferred administration dosage is within 1-50 mg/kg body weight/day.

SPECIFIC MODE OF CARRYING OUT THE INVENTION

The following examples are for illustrative purposes only and do not intend to construct a limitation for this invention in any manner.

EXAMPLE 1

Preparation of a Chloroform Extract a. Culture of Seeds of fungi *Marasmius androsaceus* L.es Fr:

A slant culture medium was prepared by mixing the following components (by weight): bran 1-10, glucose 0.3-3, peptone 0.2-2, magnesium sulfate 0.01-0.1, potassium dihydrogen sulfate 0.02-0.2, agar 0.5-5 and water 100. Then, a strain was inoculated to the slant plane and cultured at 20-30° C. for 10-20 days.

b. Fermentation Culture of fungi *Marasmius androsaceus* L.es Fr:

A culture medium was prepared by mixing the following components (by weight): bran 3-30%, glucose 1-10%, corn slurry liquid 0.2-20%, magnesium sulfate 0.01-8%, and potassium dihydrogen sulfate 0.05-9%. The slant strain is transferred to the fermentation culture medium, and cultured by fermentation at 20-30° C. for 5-10 days until forming sericate hypha, and the culture medium becoming faint yellow. The culture was stopped at pH=1.5-6.0, and then the fermentation broth is allowed to stand by for 5-10 days.

c. The fermentation broth as above obtained was filtered to obtain mycelium. After crushing, 1,000 g of the mycelium passed through a sieve of 30-40 meshes, and then was extracted with 3-5 folds of water for 5 times. The obtained extractive was recovered at low temperature and reduced pressure. The residue was dissolved with 10% NaOH, and then extracted with 3-5 folds of chloroform for 5 times. After recovering chloroform, 3 g of chloroform extract was obtained.

d. The chloroform extract was in deep brown, insoluble in water, and easily soluble in organic solvent such as chloroform, ethanol and acetone, and exhibited positive in alkaloid reaction and for phenol sulfate. By TLC detection using chloroform:methanol:ammonia water=9:1:0.1 as developing agent, five spots were observed, which $R_f$ values were respectively 0.12, 0.23, 0.45, 0.56 and 0.71, wherein the substance corresponding to the spot of $R_f$=0.56 was just the compound of formula II of the present invention.

EXAMPLE 2

Preparation of a Compound of Formula II(3,3,5,5-tetramethyl-4-piperidone)

The chloroform extract obtained in step c of Example 1 was separated with a silica gel column using chloroform:methanol:ammonia water=9:1:0.1 as developing agent. The eluents containing the compound of formula II were combined and concentrated to obtain a compound monomer of formula II.

The compound of formula II was a white needle crystal, with a melting point of 54-57° C. (decomposition).

Elemental analysis $C_9H_{17}NO$

|  | C(%) | H(%) | O(%) |
|---|---|---|---|
| Analysis values | 69.48 | 10.96 | 10.12 |
| Calculated values | 69.68 | 10.97 | 10.32 |

MS(+FAB)m/z: 156.2, 149.2, 102.2, 98.2, 83.1, 74.0, by which the compound was verified as having a molecular weight of 155.

IR(KBr)cm$^{-1}$: 3318.93, 2910.09, 2755.81, 1727.93, 1626.67, 1726, 170, 1727.93, 1626.67, 1726.23, 2317.05, 2997-2465.

UV $\lambda^{MeOH}_{MAX}$nm 264.3 ($\epsilon$13256).

$^1$H-NMR DMSO TMS $\delta$ppm 1.48(S, 12H,$(CH_3)_4$) 2.63(S, 4H,$(CH_2)_2$) 9.67(S, 1H, NH).

$^{13}$C-NMR (DMSO-D$_6$, TMS) $\delta$ppm: 27.20$(CH_3)_4$, 49.79$(CH_2)_2$, 59.09(C), 204.35(C=O).

$^1$H-$^{13}$C HMQC   $^1$H-$^{13}$C HMBC (long distance correlative) and data ascribed thereto were listed in Table 1.

TABLE 1

Data of the compound of formula II as determined at 400 MHz

| Position of C | δH(J in Hz ppm) | δC(ppm) | HMQC | HMBC |
|---|---|---|---|---|
| 1 | 9.67(S, 1H, NH) | | | |
| 2 | 2.63(S, 2H, CH$_2$) | 59.09(C) | Correlative with H at 2-position | Correlative with H at 3'-position |
| 3 | | 49.79(CH$_2$)$_2$ | | Correlative with H at 3'-position |

TABLE 1-continued

Data of the compound of formula II as determined at 400 MHz

| Position of C | δH(J in Hz ppm) | δC(ppm) | HMQC | HMBC |
|---|---|---|---|---|
| 3' | 1.48(S, 6H, (CH$_3$)$_2$) | 27.20(CH$_3$)$_2$ | Correlative with H at 3'-position | Correlative with H at 2-position Correlative with H at 3'-position Correlative with H at 2-position |
| 4 | | 204.35(C=O) | | Correlative with H at 3'-position Correlative with H at 2-position |
| 5 | | 49.79(CH$_2$)$_2$ | | |
| 5' | 1.48(S, 6H, (CH$_3$)$_2$) | 27.20(CH$_3$)$_2$ | | Correlative with H at 5'-position Correlative with H at 6-position |
| 6 | 2.63(S, 2H, CH$_2$) | 59.09(C) | | Correlative with H at 5'-position |

EXAMPLE 3

Preparation of 1-ethyl-3,3,5,5-tetramethyl-4-piperidone (Compound of Formula Ia)

0.3 g (1.94 mmol) of the compound of formula II obtained in Example 2 and 7.5 mmol of bromoethane were dissolved with 40 mol of anhydrous ethanol. The solution was charged to a 100 ml three-neck flask equipped with a reflux condenser, a stirrer, an internal thermometer and a dropping funnel. An ethanol solution containing 8.5 mmol sodium ethoxide was added to the flask with stirring followed by reacting the system at 50° C. for 20-50 min. After cooling down, 20 ml of chloroform was dropped to the system before standing by for a certain time. The resultant product was filtered to remove sodium bromide, and the filtrate was concentrated to dry under vacuum condition. Then, the reaction product was separated with a silica gel column, and eluted using chloroform:methanol (5:1), thereby obtaining the titled compound of formula Ia: 1-ethyl-3,3,5,5-tetramethyl-4-piperidone.

FAB-MS m/z: 185[M+H]$^+$, by which the compound was verified as having a molecular weight of 184.

EXAMPLE 4

Preparation of 3,3,5,5-tetramethyl-4-piperidanol (Compound of Formula Ib)

0.5 g (3.22 mmol) of the compound of formula II obtained in Example 2 was dissolved with 50 ml chloroform. The obtained solution was charged to a three-neck flask equipped with a reflux condenser, a stirrer and an internal thermometer. Sodium borohydride as a reducing agent was added in an equal mole to the solution before allowing the system to react at 50° C. for 100-120 min. The resultant product was filtered to remove the reducing agent, and the filtrate was concentrated to dry under vacuum condition. Then, the reaction product was separated with a silica gel column, and eluted using chloroform:methanol (5:1), thereby obtaining the titled compound of formula Ib: 3,3,5,5-tetramethyl-4-piperidanol.

FAB-MS m/z: 158[M+H]$^+$, by which the compound was verified as having a molecular weight of 157.

EXAMPLE 5

Preparation of a Hydrochloric Acid Salt of the Compound of Formula II 1 g (6.45 mmol) of the compound of formula II obtained in Example 2 was charged to a 300 ml three-neck round flask equipped with a reflux condenser, a stirrer, an internal thermometer and a dropping funnel. In a water bath of 80° C., the compound was completely dissolved by adding 100 ml acetone with stirring and thereafter a 6N HCl solution in an equal mole was slowly dropped to the solution. After finishing the dropping, the system is allowed to stand by for 10 min before recovering acetone till dry. The residue was dissolved with 30 ml chloroform followed by filtering, and then a 10 ml ethyl acetate solution was added to the filtrate. After standing by for 5 h, the solution was filtered and crystallized, thereby obtaining the titled hydrochloric acid salt of the compound of formula II: 3,3,5,5-tetramethyl-4-piperidone hydrochloride.

EXAMPLE 6

Effects of the Chloroform Extract, the Compound of Formula II and the Compound of Formula Ib on Ileum Smooth Muscle of Guinea Pig About 0.5 g of the chloroform extract, the compound of formula II or the compound of formula Ib was exactly weighted, and dissolved with distilled water to obtain a sample solution of about 10 mg/ml. An ileum of guinea pig is collected and is flushed with a pre-cooled Tai's nutrient solution (which comprised of 1000 ml water, 8 g NaCl, 0.2 g KCl, 0.1 g MgCl$_2$, 0.05 g NaH$_2$PO$_4$, 1 g NaHCO$_3$, 0.2 g CaCl$_2$ and 1 g glucose with pH=7.4) to remove food residue therein, and then said ileum is cut into a section of 3 cm long. The section was clamped at its both ends with frog heart clips, and placed in a perfusion tank with the lower end being fixed at the bottom of the tank and the top end being connected by a thread to a tensile transducer of a two-way electrophysiolograph, so that the automatic rhythmic contraction of the ileum section was recorded. The Tai's nutrient solution in the tank was kept at a temperature of 35° C., into which pure nitrogen was bubbled. The ileum section was exerted with 1 g of pulling force when being fixed, and its contraction was recorded after balancing for 40 min, during which the Tai's nutrient solution was changed once per 20 min. The normal contraction curve of the ileum section was firstly recorded using isoprenaline as a positive control. Then, the contraction curves of the ileum section were recorded after adding the chloroform extract, the compound of formula II or the compound of formula Ib of different concentrations respectively. The results were shown in Table 2.

TABLE 2

Effects of different samples on ileum smooth muscle of guinea pig

| Name of Sample | Concentration (mg/ml) | Time of taking effect (min) | Relaxation Time(h) |
|---|---|---|---|
| Isoprenaline | $5 \times 10^{-5}$ | 16 | 0.3 |
| Chloroform extract | $5 \times 10^{-3}$ | 3 | 5 |
| Compound of formula II | $1 \times 10^{-4}$ | 2 | 7 |
| Compound of formula Ib | $1 \times 10^{-4}$ | 3 | 5 |

The experimental results showed that: all the chloroform extract, the compound of formula II and the compound of formula Ib of different concentrations could inhibit the automatic rhythmic contraction of the ileum section. The chloroform extract at a final concentration of $5 \times 10^{-3}$ as well as the compound of formula II or the compound of formula Ib at a concentration of $1 \times 10^{-4}$ could slowly relax the smooth muscle. The contraction of the smooth muscle could completely disappear after 2-3 min, and the relaxation of the smooth muscle could continue for 5-7 h (flushing once per 15 min). In contrast, the contraction of the smooth muscle inhibited by isoprenaline as a positive control at a concentration of $5 \times 10^{-5}$ mg/ml was resumed in 20 min after flushing. The result indicates that the chloroform extract, the compound of formula II and the compound of formula Ib could take effect for a far longer time than the positive control.

EXAMPLE 7

Effects of the Chloroform Extract, the Compound of Formula II and the Compound of Formula Ia on Aorta of Rabbit A New Zealand rabbit was beheaded and unconscious. After thoracotomy, its thoracic aorta was quickly taken out, and quickly placed in and flushed with a pre-cooled LOCK's solution (which comprised of 1000 ml water, 9 g NaCl, 0.35 g KCl, 0.35 g $MgSO_4.7H_2O$, 0.16 g $KH_2PO_4$, and 1 g $NaHCO_3$) to remove bloodiness. The connective tissue outside the blood vessel was carefully cut off, and an aorta section of 2-3 mm wide at an angle of 45° relative to the vessel was taken for use in the following test.

The aorta section of 2 cm long was clamped at its both ends with frog heart clips, and put in a thermostatic perfusion tank of 38° C. with the lower end being fixed at the bottom of the tank and the top end being connected by a thread to a tensile transducer of a two-way electrophysiolograph. Oxygen was bubbled to the solution in the perfusion tank, and the contraction force of the aorta section was recorded after balancing it in the solution for 80 min. During which, the LOCK's solution was changed once per 20 min. After adding $1.2 \times 10^{-6}$ mg/ml adrenalin to the solution, the contraction curve of the aorta section was recorded. When the contraction height did not ascend anymore, the aorta section was flushed for 4 times. After 40 min, when the contraction of the aorta section was resumed, the chloroform extract, the compound of formula II or the compound of formula Ia of different concentrations was added and took effect for 10 min, followed by adding adrenalin at a concentration of $1.2 \times 10^{-6}$ mg/ml. It was observed that adrenalin added here could resume the contraction force of the aorta section only to ½-⅓ of the original value. The results were listed in Table 3.

TABLE 3

Effects of different samples on aorta of rabbit

| Name of Sample | Concentration (mg/ml) | Time of taking effect (min) | Contraction force |
|---|---|---|---|
| Isoprenaline | $1.2 \times 10^{-6}$ | 16 | 1 |
| chloroform extract | $5 \times 10^{-3}$ | 3 | 0.5 |
| compound of formula II | $1 \times 10^{-4}$ | 2 | 0.3 |
| compound of formula Ia | $1 \times 10^{-4}$ | 3 | 0.3 |

The results demonstrated that the chloroform extract, the compound of formula II or the compound of formula Ia within a concentration range of $5 \times 10^{-3}$-$1 \times 10^{-4}$ mg/ml could obviously reduce the contraction of aorta section caused by adrenalin.

EXAMPLE 8

Effects of the Chloroform Extract, the Compound of Formula II, the Hydrochloric Acid Salt of the Compound of Formula II as Well as the Compound of Formula Ib on the Reduction of Blood Pressure of Rat A spontaneously hypertensive rat (SHR) was anesthetized with 40 mg/ml pentobarbital, and fixed by its back on an experimental stand. The skin at its neck was cut open after removing hair, and thereafter the right common carotid artery was separated with its proximal end being clamped by a artery clamp and its axifugal end being ligated by a thread. A V-shape cut was made with scissors at the axifugal end, into which an arterial cannula filled with heparin physiological saline was inserted. The arterial cannula was connected with a blood pressure transducer, and then the blood pressure transducer was connected to a computer-controlled three-way physiological-pharmacological recorder. The right femoral vein of the rat was separated and intubated for the injection of a drug. When the blood pressure became stable (i.e., the blood pressure contraction curve became straight), the rat was administered by intravenous route. The results were shown in Table 4.

TABLE 4

Effects of the chloroform extract, the compound of formula II and the compound of formula Ib on the reduction of blood pressure of SHR rat

| Drug | Dosage (mg/kg) | Blood pressure (mm/Hg) | Before administration | \multicolumn{4}{c}{Time after administration (min)} | | | |
|---|---|---|---|---|---|---|---|
| | | | | 5 | 60 | 120 | 240 |
| Chloroform extract | 200 | Systolic pressure | 179 ± 10 | 145 ± 12* | 124 ± 10** | 125 ± 9.6** | 162 ± 12** |
| | | Diastolic pressure | 129 ± 16 | 107 ± 13* | 88 ± 1** | 87 ± 13** | 113 ± 10** |
| Compound of formula II | 10 | Systolic pressure | 174 ± 11 | 141 ± 9.2* | 120 ± 12 | 125 ± 14** | 163 ± 12** |
| | | Diastolic pressure | 124 ± 12 | 105 ± 11* | 84 ± 11** | 83 ± 21** | 110 ± 18** |
| Hydrochloric acid salt of compound of formula II | 10 | Systolic pressure | 170 ± 9.3 | 139 ± 19* | 123 ± 11 | 129 ± 17** | 169 ± 14** |
| | | Diastolic pressure | 119 ± 15 | 109 ± 13* | 89 ± 12** | 80 ± 23** | 112 ± 16** |
| Compound of formula Ib | 10 | Systolic pressure | 178 ± 13 | 140 ± 19* | 121 ± 15** | 126 ± 16** | 162 ± 11** |
| | | Diastolic pressure | 125 ± 17 | 1099 ± 1* | 88 ± 10** | 89 ± 8.9** | 107 ± 9.2** |

*□P < 0.05 in comparison with that before administration.
**□P < 0.01 in comparison with that before administration.

The experimental results demonstrated that all the chloroform extract, the compound of formula II, the hydrochloric acid salt of the compound of formula II as well as the compound of formula Ib within a dosage range of 10-200 mg/kg could obviously reduce the systolic pressure and diastolic pressure of SHR rat.

EXAMPLE 9

Effects of the Chloroform Extract, the Compound of Formula I and the Compound of Formula Ib on the Reduction of Blood Pressure of Cat Five cats of 2.5-3.2 kg were administered orally and intravenously respectively according to the method in Example 8, and then their systolic pressure and diastolic pressure were determined using normal cats non-administered as a control group. The results showed that all the compounds have very notable effects on the reduction of blood pressure (see Tables 5-9).

TABLE 5

Blood pressure values of cats as a control group

| Sample, Time | Animal 1 Systolic pressure (mmHg) | Animal 2 Systolic pressure (mmHg) | Animal 3 Systolic pressure (mmHg) | Animal 4 Systolic pressure (mmHg) | Animal 5 Systolic pressure (mmHg) | Average Systolic pressure (mmHg) | Standard derivation | T value | P value |
|---|---|---|---|---|---|---|---|---|---|
| Control group | | | | | | | | | |
| Before administration | 168 | 212 | 200 | 182 | 184 | 189.2 | 17.06458 | | |
| 10 min after administration | 168 | 212 | 195 | 183 | 187 | 189 | 16.17096 | 0.985289 | |
| 20 min after administration | 162 | 206 | 195 | 184 | 187 | 186.8 | 16.2696 | 0.825656 | |
| 30 min after administration | 168 | 212 | 203 | 180 | 173 | 187.2 | 19.27952 | 0.866419 | |
| 40 min after administration | 162 | 203 | 215 | 179 | 173 | 186.4 | 21.92715 | 0.827366 | |

TABLE 5-continued

Blood pressure values of cats as a control group

| | | | | | | | | |
|---|---|---|---|---|---|---|---|---|
| 50 min after administration | 160 | 190 | 215 | 172 | 173 | 182 | 21.31901 | 0.571749 |
| 60 min after administration | 160 | 210 | 190 | 172 | 178 | 182 | 19.0263 | 0.546305 |

| | Animal 1 Diastolic pressure (mmHg) | Animal 2 Diastolic pressure (mmHg) | Animal 3 Diastolic pressure (mmHg) | Animal 4 Diastolic pressure (mmHg) | Animal 5 Diastolic pressure (mmHg) | Average Diastolic pressure (mmHg) | Standard derivation | T value | P value |
|---|---|---|---|---|---|---|---|---|---|
| Before administration | 144 | 131 | 125 | 148 | 156 | 140.8 | 12.63725 | | |
| 10 min after administration | 136 | 136 | 125 | 150 | 156 | 140.6 | 12.36123 | 0.980437 | |
| 20 min after administration | 137 | 136 | 125 | 150 | 153 | 140.2 | 11.38859 | 0.939077 | |
| 30 min after administration | 133 | 120 | 125 | 148 | 156 | 136.4 | 15.24139 | 0.632606 | |
| 40 min after administration | 133 | 120 | 125 | 153 | 160 | 138.2 | 17.51285 | 0.794587 | |
| 50 min after administration | 135 | 120 | 120 | 153 | 155 | 136.6 | 17.03819 | 0.669695 | |
| 60 min after administration | 136 | 124 | 120 | 148 | 160 | 137.6 | 16.63731 | 0.74081 | |

TABLE 6

Effect of the chloroform extract (oral administration) on the reduction of blood pressure of cats

| Sample, Time | Animal 1 Systolic pressure (mmHg) | Animal 2 Systolic pressure (mmHg) | Animal 3 Systolic pressure (mmHg) | Animal 4 Systolic pressure (mmHg) | Average Systolic pressure (mmHg) | Standard derivation | T value | P value |
|---|---|---|---|---|---|---|---|---|
| Chloroform extract 100 mg/kg o.s | | | | | | | | |
| Before administration | 200 | 205 | 216 | 183 | 201 | 13.7356 | | 0.300196 |
| 10 min after administration | 193 | 190 | 206 | 176 | 191.25 | 12.31192 | 0.331138 | 0.825362 |
| 20 min after administration | 173 | 207 | 190 | 161 | 182.75 | 20.07278 | 0.184113 | 0.74712 |
| 30 min after administration | 143 | 181 | 176 | 153 | 163.25 | 18.19112 | 0.01616 | 0.099648 |
| 40 min after administration | 129 | 162 | 170 | 132 | 148.25 | 20.79062 | 0.005477 | 0.032864 |
| 50 min after administration | 127 | 162 | 171 | 133 | 148.25 | 21.53099 | 0.006141 | 0.051095 |
| 60 min after administration | 126 | 161 | 176 | 135 | 149.5 | 23.07235 | 0.0086 | 0.053166 |
| 90 min after administration | 127 | 175 | 183 | 136 | 155.25 | 27.86126 | 0.025759 | |
| 120 min after administration | 145 | 175 | 184 | 146 | 162.5 | 19.97498 | 0.019165 | |
| 150 min after administration | 188 | 183 | 186 | 171 | 182 | 7.615773 | 0.051897 | |
| 180 min after administration | 196 | 201 | 206 | 179 | 195.5 | 11.73314 | 0.564903 | |

| | Animal 1 Diastolic pressure (mmHg) | Animal 2 Diastolic pressure (mmHg) | Animal 3 Diastolic pressure (mmHg) | Animal 4 Diastolic pressure (mmHg) | Average Diastolic pressure (mmHg) | Standard derivation | T value | P value |
|---|---|---|---|---|---|---|---|---|
| Before administration | 138 | 135 | 141 | 138 | 138 | 2.44949 | | 0.679493 |
| 10 min after administration | 130 | 140 | 157 | 130 | 139.25 | 12.73774 | 0.853524 | 0.876878 |
| 20 min after administration | 115 | 140 | 137 | 125 | 129.25 | 11.5 | 0.187228 | 0.196542 |

TABLE 6-continued

Effect of the chloroform extract (oral administration) on the reduction of blood pressure of cats

| 30 min after administration | 91 | 139 | 126 | 115 | 117.75 | 20.35313 | 0.095604 | 0.158499 |
|---|---|---|---|---|---|---|---|---|
| 40 min after administration | 83 | 114 | 120 | 98 | 103.75 | 16.66083 | 0.006593 | 0.020113 |
| 50 min after administration | 88 | 114 | 117 | 97 | 104 | 13.83233 | 0.002879 | 0.01765 |
| 60 min after administration | 85 | 120 | 116 | 97 | 104.5 | 16.42153 | 0.006839 | 0.020448 |
| 90 min after administration | 93 | 122 | 122 | 98 | 108.75 | 15.43535 | 0.009587 | |
| 120 min after administration | 109 | 122 | 134 | 116 | 120.25 | 10.59481 | 0.01715 | |
| 150 min after administration | 145 | 135 | 134 | 134 | 137 | 5.354126 | 0.74567 | |
| 180 min after administration | 151 | 143 | 142 | 135 | 142.75 | 6.551081 | 0.223219 | |

TABLE 7

Effects of the compound of formula II (oral administration) on the reduction of blood pressure of cats

| Sample, time | Animal 1 Systolic pressure (mmHg) | Animal 2 Systolic pressure (mmHg) | Animal 3 Systolic pressure (mmHg) | Animal 4 Systolic pressure (mmHg) | Average Systolic pressure (mmHg) | Standard derivation | T value | P value |
|---|---|---|---|---|---|---|---|---|
| Compound of formula II 10 mg/kg o.s | | | | | | | | |
| Before administration | 191 | 215 | 196 | 208 | 202.5 | 10.96966 | | 0.221212 |
| 10 min after administration | 190 | 180 | 159 | 136 | 166.25 | 23.9496 | 0.033194 | 0.131804 |
| 20 min after administration | 170 | 181 | 138 | 123 | 153 | 27.06782 | 0.014681 | 0.052155 |
| 30 min after administration | 154 | 140 | 138 | 130 | 140.5 | 9.983319 | 0.000159 | 0.00332 |
| 40 min after administration | 146 | 133 | 143 | 140 | 140.5 | 5.567764 | 5.54E−05 | 0.004985 |
| 50 min after administration | 149 | 140 | 144 | 144 | 144.25 | 3.685557 | 5.57E−05 | 0.010642 |
| 60 min after administration | 149 | 153 | 130 | 144 | 144 | 10.03328 | 0.000223 | 0.008944 |
| 90 min after administration | 154 | 180 | 154 | 140 | 157 | 16.69331 | 0.003868 | |
| 120 min after administration | 146 | 195 | 163 | 156 | 165 | 21.18175 | 0.019962 | |
| 150 min after administration | 146 | 206 | 168 | 157 | 169.25 | 26.09438 | 0.057113 | |
| 180 min after administration | 158 | 213 | 170 | 164 | 176.25 | 24.985 | 0.102697 | |
| 210 min after administration | 159 | 213 | 170 | 164 | 176.5 | 24.74537 | 0.103109 | |
| 240 min after administration | 178 | 213 | 176 | 164 | 182.75 | 21.09305 | 0.147696 | |

| | Animal 1 Diastolic pressure (mmHg) | Animal 1 Diastolic pressure (mmHg) | Animal 1 Diastolic pressure (mmHg) | Animal 1 Diastolic pressure (mmHg) | Average Diastolic pressure (mmHg) | Standard derivation | T value | P value |
|---|---|---|---|---|---|---|---|---|
| Before administration | 143 | 165 | 145 | 137 | 147.5 | 12.15182 | | 0.448148 |
| 10 min after administration | 143 | 145 | 112 | 76 | 119 | 32.4037 | 0.150646 | 0.207389 |
| 20 min after administration | 130 | 136 | 91 | 72 | 107.25 | 30.82613 | 0.051199 | 0.060186 |
| 30 min after administration | 110 | 108 | 91 | 75 | 96 | 16.39105 | 0.002338 | 0.006499 |

TABLE 7-continued

Effects of the compound of formula II (oral administration) on the reduction of blood pressure of cats

| | | | | | | | | |
|---|---|---|---|---|---|---|---|---|
| 40 min after administration | 107 | 100 | 95 | 79 | 95.25 | 11.89888 | 0.000851 | 0.004198 |
| 50 min after administration | 110 | 116 | 95 | 83 | 101 | 14.89966 | 0.00289 | 0.013399 |
| 60 min after administration | 110 | 117 | 102 | 83 | 103 | 14.67424 | 0.003427 | 0.013881 |
| 90 min after administration | 102 | 120 | 97 | 96 | 103.75 | 11.14675 | 0.001819 | |
| 120 min after administration | 93 | 154 | 96 | 90 | 108.25 | 30.5982 | 0.054443 | |
| 150 min after administration | 93 | 161 | 109 | 84 | 111.75 | 34.42262 | 0.097877 | |
| 180 min after administration | 107 | 164 | 112 | 87 | 117.5 | 32.82783 | 0.137348 | |

TABLE 8

Effect of the compound of formula II (intravenous administration) on the reduction of blood pressure of cats

| Sample, time | Animal 1 Systolic pressure (mmHg) | Animal 2 Systolic pressure (mmHg) | Animal 3 Systolic pressure (mmHg) | Animal 4 Systolic pressure (mmHg) | Average Systolic pressure (mmHg) | Standard derivation | T value | P value |
|---|---|---|---|---|---|---|---|---|
| Compound of formula II 5 mg/kg iv | | | | | | | | |
| Before administration | 226 | 183 | 211 | 178 | 199.5 | 22.86919 | | 0.462627 |
| 10 min after administration | 100 | 110 | 182 | 150 | 135.5 | 37.78448 | 0.027401 | 0.023299 |
| 20 min after administration | 111 | 126 | 172 | 150 | 139.75 | 26.83747 | 0.014691 | 0.013666 |
| 30 min after administration | 119 | 137 | 173 | 136 | 141.25 | 22.72114 | 0.01118 | 0.013315 |
| 40 min after administration | 134 | 137 | 172 | 135 | 144.5 | 18.37571 | 0.009515 | 0.01859 |
| 50 min after administration | 156 | 147 | 171 | 135 | 152.25 | 15.17399 | 0.013747 | 0.051646 |
| 60 min after administration | 174 | 142 | 174 | 142 | 158 | 18.47521 | 0.030228 | 0.098648 |
| 90 min after administration | 170 | 167 | 178 | 143 | 164.5 | 15.06652 | 0.043138 | |
| 120 min after administration | 182 | 167 | 202 | 147 | 174.5 | 23.27373 | 0.176318 | |
| 150 min after administration | 186 | 170 | 202 | 150 | 177 | 22.2411 | 0.208039 | |
| 180 min after administration | 187 | 176 | 212 | 165 | 185 | 20.11633 | 0.377789 | |

| | Animal 1 Diastolic pressure (mmHg) | Animal 2 Diastolic pressure (mmHg) | Animal 3 Diastolic pressure (mmHg) | Animal 4 Diastolic pressure (mmHg) | Average Diastolic pressure (mmHg) | Standard derivation | T value | P value |
|---|---|---|---|---|---|---|---|---|
| Before administration | 169 | 138 | 163 | 115 | 146.25 | 24.78407 | | 0.679085 |
| 10 min after administration | 84 | 93 | 146 | 101 | 106 | 27.556 | 0.072856 | 0.038731 |
| 20 min after administration | 79 | 109 | 137 | 98 | 105.75 | 24.24012 | 0.058123 | 0.024881 |
| 30 min after administration | 80 | 111 | 136 | 98 | 106.25 | 23.55667 | 0.057871 | 0.052244 |
| 40 min after administration | 100 | 111 | 134 | 97 | 110.5 | 16.78293 | 0.054118 | 0.047452 |
| 50 min after administration | 117 | 120 | 134 | 97 | 117 | 15.25341 | 0.091131 | 0.116098 |
| 60 min after administration | 131 | 120 | 130 | 92 | 118.25 | 18.19112 | 0.118371 | 0.139775 |

TABLE 8-continued

Effect of the compound of formula II (intravenous administration) on the reduction of blood pressure of cats

| | | | | | | | |
|---|---|---|---|---|---|---|---|
| 90 min after administration | 122 | 129 | 144 | 92 | 121.75 | 21.85368 | 0.188616 |
| 120 min after administration | 123 | 129 | 148 | 96 | 124 | 21.49419 | 0.223773 |
| 150 min after administration | 124 | 140 | 148 | 98 | 127.5 | 22.05297 | 0.301473 |
| 180 min after administration | 123 | 148 | 156 | 108 | 133.75 | 22.18671 | 0.480745 |

TABLE 9

Effect of the compound of formula Ib (oral administration) on the reduction of blood pressure of cats

| Sample, time | Animal 1 Systolic pressure (mmHg) | Animal 2 Systolic pressure (mmHg) | Animal 3 Systolic pressure (mmHg) | Animal 4 Systolic pressure (mmHg) | Average Systolic pressure (mmHg) | Standard derivation | T value | P value |
|---|---|---|---|---|---|---|---|---|
| Compound of formula Ib 10 mg/kg o.s | | | | | | | | |
| Before administration | 150 | 209 | 185 | 237 | 195.25 | 36.89964 | | 0.170789 |
| 10 min after administration | 136 | 139 | 145 | 147 | 141.75 | 5.123475 | 0.028345 | 0.566023 |
| 20 min after administration | 146 | 125 | 153 | 136 | 140 | 12.19289 | 0.029435 | 0.52967 |
| 30 min after administration | 146 | 126 | 154 | 136 | 140.5 | 12.15182 | 0.03041 | 0.515824 |
| 40 min after administration | 140 | 126 | 154 | 136 | 139 | 11.6046 | 0.027038 | 0.322939 |
| 50 min after administration | 136 | 130 | 150 | 130 | 136.5 | 9.433981 | 0.021523 | 0.056753 |
| 60 min after administration | 140 | 122 | 152 | 138 | 138 | 12.32883 | 0.025844 | 0.000905 |
| 90 min after administration | 135 | 130 | 156 | 146 | 141.75 | 11.61536 | 0.032596 | |
| 120 min after administration | 146 | 131 | 165 | 164 | 151.5 | 16.21727 | 0.072973 | |
| 150 min after administration | 145 | 139 | 166 | 171 | 155.25 | 15.6285 | 0.092893 | |
| 180 min after administration | 152 | 142 | 160 | 180 | 158.5 | 16.11418 | 0.117733 | |
| 210 min after administration | | | 156 | 186 | 171 | 21.2132 | 0.452377 | |
| 240 min after administration | | | 155 | 202 | 178.5 | 33.23402 | 0.619755 | |

| Sample, time | Animal 1 Diastolic pressure (mmHg) | Animal 2 Diastolic pressure (mmHg) | Animal 3 Diastolic pressure (mmHg) | Animal 4 Diastolic pressure (mmHg) | Average Diastolic pressure (mmHg) | Standard derivation | T value | P value |
|---|---|---|---|---|---|---|---|---|
| Before administration | 134 | 156 | 116 | 154 | 140 | 18.8326 | | 0.949541 |
| 10 min after administration | 119 | 105 | 100 | 103 | 106.75 | 8.421203 | 0.018057 | 0.019637 |
| 20 min after administration | 135 | 89 | 104 | 89 | 104.25 | 21.68525 | 0.047198 | 0.398951 |
| 30 min after administration | 130 | 90 | 109 | 90 | 104.75 | 19.06786 | 0.039029 | 0.939613 |
| 40 min after administration | 126 | 91 | 102 | 90 | 102.25 | 16.74067 | 0.024122 | 0.877248 |
| 50 min after administration | 126 | 96 | 103 | 87 | 103 | 16.67333 | 0.02588 | 0.902185 |
| 60 min after administration | 123 | 97 | 102 | 114 | 109 | 11.74734 | 0.031441 | 0.980271 |
| 90 min after administration | 125 | 95 | 110 | 107 | 109.25 | 12.33896 | 0.034116 | |

TABLE 9-continued

Effect of the compound of formula Ib (oral administration) on the reduction of blood pressure of cats

| 120 min after administration | 131 | 94 | 115 | 127 | 116.75 | 16.62077 | 0.113592 |
| 150 min after administration | 132 | 98 | 117 | 120 | 116.75 | 14.08013 | 0.09535 |
| 180 min after administration | 133 | 97 | 113 | 131 | 118.5 | 16.92139 | 0.14035 |

The invention claimed is:

1. A method for preparing *Marasmius androsaceus* L.es Fr extract, which comprises extracting fungi *Marasmius androsaceus* L.es Fr with an organic solvent, an aqueous organic solvent or water, and concentrating the obtained extractive.

2. The method of claim 1, wherein the organic solvent is methanol, ethanol, propanol, butanol, dichloromethane, trichloromethane, methyl acetate, ethyl acetate, petroleum or diethyl ether.

3. A method for preparing a compound of the following Formula I or a pharmaceutically acceptable salt thereof:

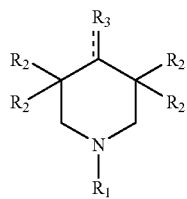

I wherein,
$R_1$ and each of $R_2$, the same or different, independently represent hydrogen atom or $C_1$-$C_5$ alkyl;
┄┄ represents a single bond or a double bond, when ┄┄ is a double bond, $R_3$ is oxygen atom; when ┄┄ is a single bond, $R_3$ is hydroxyl group, which comprises extracting fungi Marasmius androsaceus L.es Fr with an organic solvent, an aqueous organic solvent or water to obtain an extract, separating and purifying the extract thereby obtaining a compound monomer of the following Formula II,

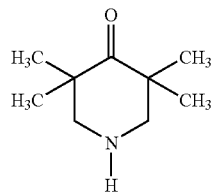

II and then deriving the compound of Formula I by reacting the compound monomer of Formula II with a calculated amount of alkyl halide under basic condition.

4. A method for treating an individual with hypertension comprising administering the compound of the following Formula I to said individual:

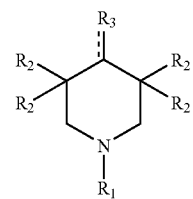

I wherein,
$R_1$ and each of $R_2$, the same or different, independently represent hydrogen atom or $C_1$-$C_5$ alkyl;
┄┄ represents a single bond or a double bond, when ┄┄ is a double bond, $R_3$ is oxygen atom; when ┄┄ is a single bond, $R_3$ is hydroxyl group.

5. A method for treating an individual with hypertension comprising administering the compound of the following Formula II to said individual:

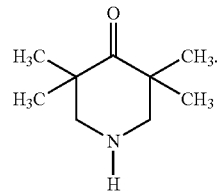

II

6. The method of claim 4 wherein said compound is 1-ethyl-3,3,5,5,-tetramethyl-4-piperidone.

7. The method of claim 4 wherein said compound is 3,3,5,5-tetramethyl-4-piperidanol.

8. The method of claim 3 wherein said compound is 1-ethyl-3,3,5,5-tetramethyl-4-piperidone.

9. The method of claim 3 wherein said compound is 3,3,5,5-tetramethyl-4-piperidanol.

* * * * *

UNITED STATES PATENT AND TRADEMARK OFFICE
CERTIFICATE OF CORRECTION

PATENT NO.       : 7,608,630 B2                                      Page 1 of 1
APPLICATION NO. : 10/587824
DATED            : October 27, 2009
INVENTOR(S)      : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this

Twelfth Day of October, 2010

David J. Kappos
*Director of the United States Patent and Trademark Office*